US007823808B2

(12) United States Patent
Yamaguchi et al.

(10) Patent No.: US 7,823,808 B2
(45) Date of Patent: *Nov. 2, 2010

(54) ELECTROSTATIC SPRAYING DEVICE

(75) Inventors: Naoki Yamaguchi, Hikone (JP); Koji Asakawa, Hikone (JP); David Edward Wilson, Reisterstown, MD (US); Shunichi Nagasawa, Nishinomiya (JP)

(73) Assignees: Panasonic Electric Works Co., Ltd., Osaka (JP); The Procter & Gamble Company, Cincinnati, OH (US)

( * ) Notice: Subject to any disclaimer, the term of this patent is extended or adjusted under 35 U.S.C. 154(b) by 16 days.

This patent is subject to a terminal disclaimer.

(21) Appl. No.: 10/588,437

(22) PCT Filed: Feb. 9, 2004

(86) PCT No.: PCT/JP2004/001357

§ 371 (c)(1),
(2), (4) Date: Aug. 7, 2006

(87) PCT Pub. No.: WO2005/075091

PCT Pub. Date: Aug. 18, 2005

(65) Prior Publication Data

US 2007/0114305 A1 May 24, 2007

(51) Int. Cl.

| | |
|---|---|
| ***B05B 5/00*** | (2006.01) |
| *A62C 13/62* | (2006.01) |
| *A62C 11/00* | (2006.01) |
| *B01D 17/00* | (2006.01) |
| *B04B 9/04* | (2006.01) |
| *A61M 11/00* | (2006.01) |
| *A61M 15/00* | (2006.01) |
| *B65D 35/28* | (2006.01) |
| *B65D 35/00* | (2006.01) |
| *B65D 1/32* | (2006.01) |
| *G01F 11/00* | (2006.01) |
| *B05B 7/00* | (2006.01) |

(52) U.S. Cl. .................... 239/690.1; 239/690; 239/692; 239/697; 239/698; 239/704; 239/705; 239/706; 239/707; 239/708; 239/302; 239/327; 239/328; 239/329; 239/330; 239/332; 128/200.14; 128/203.12; 222/103; 222/107; 222/386.5; 222/630

(58) Field of Classification Search ................ 239/690, 239/706, 708, 690.1, 302, 328, 332, 308, 239/316, 303–305, 327, 329, 330, 692, 697–698, 239/704, 705, 707; 128/203.12, 200.14; 222/103, 107, 386.5, 630; 95/71; 347/55
See application file for complete search history.

(56) References Cited

U.S. PATENT DOCUMENTS

| | | | | |
|---|---|---|---|---|
| 2,525,347 | A * | 10/1950 | Gilman | 95/71 |
| 3,608,823 | A * | 9/1971 | Buschor | 239/698 |
| 3,747,850 | A * | 7/1973 | Hastings et al. | 239/3 |
| 3,887,928 | A * | 6/1975 | Ohno et al. | 347/55 |
| 4,069,974 | A * | 1/1978 | Zawacki | 239/706 |
| 4,962,885 | A * | 10/1990 | Coffee | 239/3 |
| 5,163,625 | A * | 11/1992 | Takayama et al. | 239/703 |
| 5,221,050 | A * | 6/1993 | Jeffries et al. | 239/708 |
| 5,337,963 | A * | 8/1994 | Noakes | 239/690 |
| 5,725,161 | A * | 3/1998 | Hartle | 239/690 |
| 5,813,614 | A * | 9/1998 | Coffee | 239/690 |
| 5,927,618 | A * | 7/1999 | Jefferies et al. | 239/690.1 |
| 6,079,634 | A * | 6/2000 | Noakes et al. | 239/3 |
| 6,311,903 | B1 * | 11/2001 | Gaw et al. | 239/690 |
| 6,318,647 | B1 * | 11/2001 | Gaw et al. | 239/690 |
| 6,328,233 | B1 * | 12/2001 | Moy et al. | 239/600 |
| 6,460,781 | B1 * | 10/2002 | Garcia et al. | 239/327 |
| 6,595,208 | B1 * | 7/2003 | Coffee et al. | 128/203.12 |
| 6,684,879 | B1 | 2/2004 | Coffee et al. | |
| 6,708,908 | B2 * | 3/2004 | Heldt et al. | 239/700 |
| 7,128,277 | B2 * | 10/2006 | Schaupp | 239/3 |
| 2001/0020652 | A1 * | 9/2001 | Kadlubowski et al. | 239/690 |
| 2001/0020653 | A1 | 9/2001 | Wilson et al. | |
| 2001/0023902 | A1 * | 9/2001 | Wilson et al. | 239/690 |
| 2001/0038047 | A1 | 11/2001 | Wilson et al. | |
| 2003/0197075 | A1 * | 10/2003 | Sano | 239/551 |

2004/0021017 A1 2/2004 Sumiyoshi et al.

FOREIGN PATENT DOCUMENTS

| | | |
|---|---|---|
| KR | 2001-99950 | 1/2001 |
| WO | WO 00/38770 | 7/2000 |
| WO | WO-02055211 A1 | 7/2002 |
| WO | WO 03/072263 A1 | 9/2003 |

OTHER PUBLICATIONS

The Examination Report Dated May 1, 2007 for Korean Patent Application No. 10-2006-7017335.

Japanese Office Action w/English language translation for Chinese Application No. 200480041493.8, mailed Dec. 14, 2007.

* cited by examiner

*Primary Examiner*—Dinh Q Nguyen
*Assistant Examiner*—Steven M Cernoch
(74) *Attorney, Agent, or Firm*—Cheng Law Group, PLLC

(57) ABSTRACT

An electrostatic spraying device having a removable cartridge with a reservoir containing a volume of liquid compositions to be electrically sprayed on a user's skin. The device includes a nozzle for dispensing the liquid as well as an emitter electrode disposed adjacent to the nozzle for charging the liquid composition just being dispensed from the nozzle. A field electrode surrounds the reservoir in order to charge the liquid composition within the reservoir, thereby avoiding an occurrence of electric current which would otherwise flow in the liquid composition and would deteriorate the composition remaining in the reservoir. The reservoir is devoid of the field electrode, and therefor can be designed into a simple and compact structure without being restricted by the field electrode, assuring to have an enhanced liquid containing volume in relation to the bulk of the removable cartridge.

17 Claims, 16 Drawing Sheets

FIG. 21
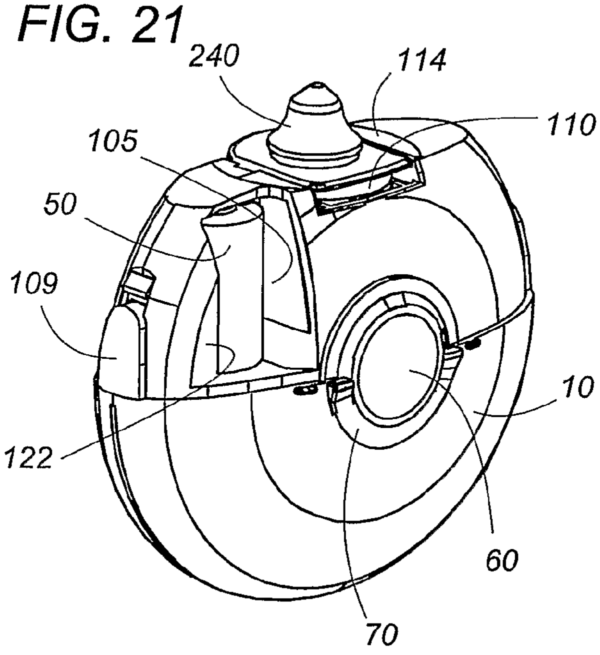
FIG. 22
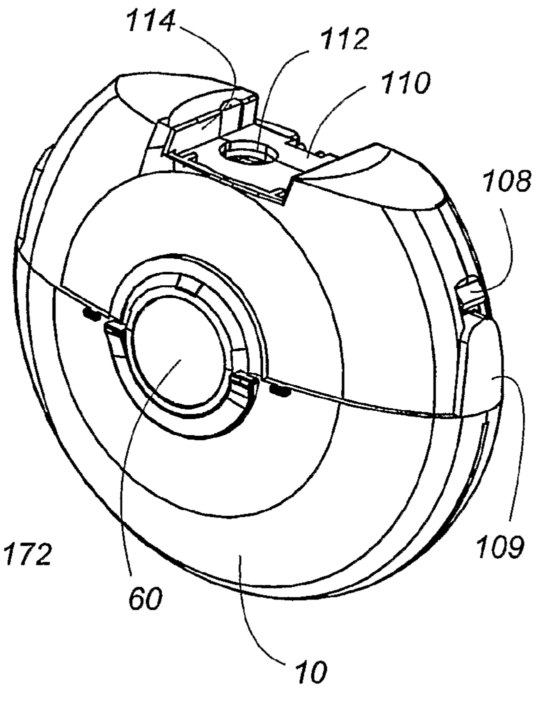
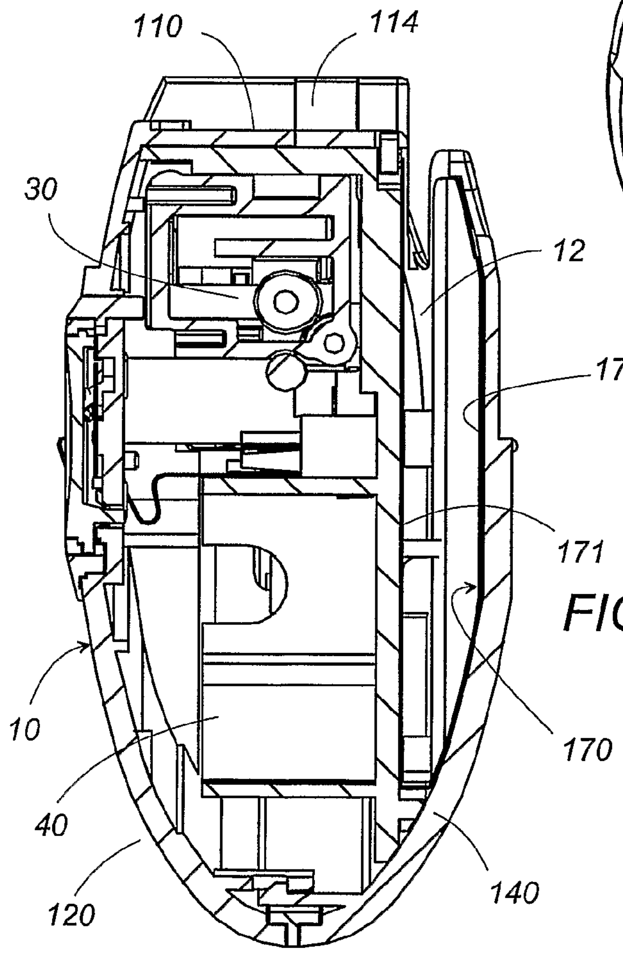
FIG. 23

ELECTROSTATIC SPRAYING DEVICE

BACKGROUND OF THE INVENTION

1. Field of the Invention

The present invention relates to an electrostatic device for personal use, and more particularly to a device for spraying a liquid composition by means of an electrostatic force.

2. Description of the Related Art

WO 03/072263 discloses an electrostatic spraying device having a removable cartridge with a reservoir containing a volume of a liquid composition. The device includes a plunger pump that displaces the liquid out of the reservoir and a nozzle for dispensing the liquid. The nozzle is provided with an emitter electrode which applies a high voltage to the composition being supplied from the reservoir to the nozzle, i.e., electrostatically charge the particles of the liquid composition for spraying the composition by the electrostatic force. Because the liquid composition within the reservoir may be deteriorated upon seeing an electrical current therein, the device is so designed to keep fresh or avoid deterioration of the liquid composition remaining in the reservoir. For this purpose, a field electrode or shield is introduced to surround the reservoir so as to supply the same electrical potential to the liquid composition advanced around the nozzle and the composition remaining in the reservoir, and therefor minimize an undesired current flowing between these zones. Although this scheme of providing the field electrode around the reservoir is suitable for keeping the liquid composition intact, the field electrode itself adds a certain bulk and complexity to the removable cartridge. Consequently, when the cartridge is desired to be sufficiently compact to be easily carried with a person, the cartridge is realized only at an expense of reducing a liquid holding capacity of the reservoir. Thus, there remains a need for making the cartridge as compact as possible, while enabling the cartridge or reservoir to hold a sufficient amount of the liquid composition without causing deterioration during use.

None of the existing art provides all of the advantages and benefits of the present invention.

SUMMARY OF THE INVENTION

The present invention is directed to an improved electrostatic spraying device which is capable of supplying an increased liquid containing volume to a removable cartridge, yet keeping the cartridge as compact as possible for enhanced handling performance. The device in accordance with the present invention is configured to electrostatically charge and dispense the liquid composition from a supply to a dispensing point, and includes an actuator, a high voltage generator to provide a high voltage, a power source to activate the actuator and the high voltage generator, a reservoir to contain the supply of the liquid composition, and a dispensing unit. The dispensing unit is provided to spray the liquid composition, and includes a pump which is located in immediate upstream relation with the reservoir for supplying the liquid composition from the reservoir, and which is mechanically connected to the actuator to be driven thereby. An emitter electrode is included in the dispensing unit to be electrically connected to the high voltage generator in order to electrostatically charge the liquid composition. Also included in the dispensing unit is a nozzle that is disposed at the dispensing point for spraying the liquid composition. The device further includes a field electrode that surrounds the reservoir and is connected to the high voltage generator so that the entire liquid composition is given more or less a common electric potential. The reservoir is configured to provide a removable cartridge. One characterizing feature of the present invention resides in that the reservoir is devoid of the field electrode. Thus, the reservoir can be designed into a simple and compact structure without being restricted by the field electrode, thereby providing an increased liquid containing volume in relation to the bulk of the removable cartridge.

In an exemplary embodiment, the device includes a housing that carries the actuator, the high voltage generator, and the power source. The housing has a concavity for detachably receiving the reservoir. It is within the concavity that the field electrode is incorporated to surround the reservoir of the cartridge. By the provision of the field electrode on the side of the housing, the reservoir can be given design flexibility and be shaped into effective configuration assuring increased liquid containing volume as well as improved appearance.

Preferably, the housing incorporates a motor which drives the actuator for operating the pump, and also incorporates a frame which mounts the motor as well as the high voltage generator. The frame divides an interior space of the housing into a front compartment and a rear compartment. The front compartment accommodates the motor as well as the high voltage generator, while the rear compartment defines the concavity for receiving the reservoir. The housing includes a front shell and a rear shell. The front shell is fitted over the frame to define therebetween the front compartment. Likewise, the rear shell is fitted over the frame to define therebetween the rear compartment. The field electrode is composed of a first plate secured to the frame, and a second place secured to the interior of the rear shell. Thus, it is readily possible to make the use of substantially the whole space between the rear shell and the frame to realize the concavity for the reservoir, which contributes to give an increased liquid containing volume to the reservoir.

Preferably, the reservoir is coupled to the dispensing unit and is cooperative therewith to define the cartridge. A positioning means is provided on the side of the housing to detachably engage the cartridge with the housing when the reservoir is placed into the concavity. When the cartridge is attached to the housing, the actuator is detachably engaged with a mechanism to activate the pump, and the emitter electrode is detachably in contact with a voltage terminal to receive the high voltage for electrostatically spraying the liquid composition. The positioning means may be realized by a mount formed at the upper end of the housing.

Preferably, the voltage terminal is located below an opening which is formed in the mount to permit the lower end of the emitter electrode to project through the opening for contact with the voltage terminal only when the dispensing unit rests on the mount. In other words, the voltage terminal bearing the high voltage can be kept away from an accidental contact with a human body for safety purpose.

The reservoir may be deformable and made of a dielectric material so that the liquid composition can be easily pumped out to a full extent.

Preferably, the pump is configured as a suction pump having a drive element which is driven by the actuator to suck up the liquid composition from the reservoir and forces it out of the nozzle. In addition to the enhanced pumping efficiency specific to the suction pump, the use of the suction pump can realize a structure in which the suction pump is located on the side of the nozzle and outwardly of the reservoir or the concavity, enabling the reservoir to occupy the full space of the concavity with the attendant share of increased liquid containing volume.

A motor may be incorporated in the housing to drive the actuator for operating the pump, and is supported by the frame. The frame is configured to divide the interior space of the housing into a front compartment and a rear compartment. The front compartment is provided to accommodate therein the motor as well as the high voltage generator, while the rear compartment defines the concavity for receiving the reservoir. With this arrangement, the concavity receiving the reservoir can be formed on one side of the housing free from the motor and the high voltage generator both of which are inherently bulky, and can be therefore designed into an optimum configuration in match with the capacity of the reservoir, which in turn enables to design the device combining aesthetic and functional appeal.

Considering that the high voltage generator includes a transformer which is inherently bulky and occupies much space, the device is advantageously designed to make the housing compact by arranging the transformer in stack with the motor within the front compartment. Further, a battery also relatively bulky may be accommodated within the front compartment for energizing the motor. Also for making the housing compact, the battery is arranged in a side-by-side relation with the motor in a direction perpendicular to a vertical axis of the housing and arranged in stack with the transformer along the vertical axis.

The device may include an inner cover which is detachably placed over a top portion of the housing and has an opening through which the nozzle extends. Defined around the opening is a retainer which is placed against a portion of the dispensing unit to hold it in position in the mount. In this connection, the housing may be provided with a positioning means for engagement with the inner cover to retain it on the housing.

In a preferred embodiment, the front shell is fitted over the frame to define therebetween the front compartment, while the rear shell is fitted on the frame to define therebetween the rear compartment. The front shell is formed with a battery opening through which the battery is placed on the frame and which is shielded by the inner cover.

Further, it is preferred to include an outer cover that fits over the inner cover for concealing therebehind the dispensing unit, a button for releasing the inner cover, and a switch knob for actuating the pump. Thus, the device can be well protected from unintended or accidental operation when fitted with the outer cover.

These and still other features, aspects, and advantages of the present invention will become more apparent from the following detailed explanation of preferred embodiments when taken in conjunction with the attached drawings.

BRIEF DESCRIPTION OF THE DRAWINGS

While the specification concludes with claims particularly pointing out and distinctly claiming the invention, it is believed that the present invention will be better understood from the following description of preferred, nonlimiting embodiments and representations taken in conjunction with the accompanying drawings in which:

FIG. 21 is a perspective view of the above device with the inner cover removed;

FIG. 22 is a perspective view of the above device shown with the cartridge and an inner cover removed;

FIG. 23 is a vertical section of the device corresponding to FIG. 22;

DETAILED DESCRIPTION OF EXEMPLARY EMBODIMENTS

Figure 1:
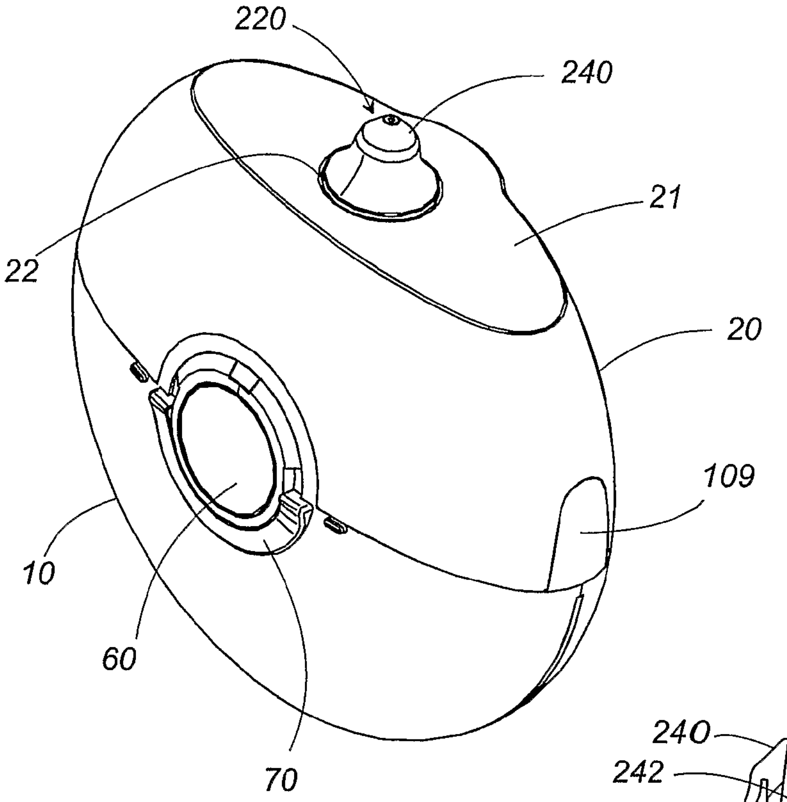
FIG. 1 is a perspective view of an electrostatic spraying device in accordance with an exemplary embodiment of the present invention.

Now referring to FIGS. 1 to 7, there is shown an electrostatic spraying device in accordance with a exemplary embodiment of the present invention. The device is configured into a self-contained portable structure that is compact enough to be easily carried with. The device is basically composed of a main body housing 10 and a removable cartridge 200 containing a volume of a liquid composition to be electrostatically sprayed according to a mechanism already disclosed in WO 01/12336, WO 01/12335, US 2001-0020653A, US 2001-0038047A, US 2001-0020652A, US 2001-0023902A, and WO 03/072263, incorporated herein by reference. The liquid composition utilized in the device include those disclosed in WO 03/072263, also incorporated herein by reference, i.e., an emulsion having conductive and insulating phases, although not limited thereto.

The housing 10 is dimensioned to be grasped by a user's hand and incorporates an electric motor 30, a high voltage generator 40, and a battery 50, i.e., a power source for activating the motor and the high voltage generator 40. The motor 30 actuates a dispensing unit 220 provided on the side of the cartridge 200 to dispense the liquid composition, while the high voltage generator 40 applies a high voltage of 1000 volts or more to the liquid composition being dispensed for electrically spraying the liquid composition on a user's. The housing 10 is formed with a concavity 12 for receiving a reservoir 210 of the cartridge 200 containing the liquid composition. In an exemplary embodiment, an inner cover 20 is detachably fitted over the upper end of the housing 10 to hold therebetween the dispensing unit 220 of the cartridge 200. In another exemplary embodiment, an outer cover 26 is detachably fitted over the inner cover 20 to conceal therebehind the dispensing unit 220 for protection thereof when the device is not in use.

The cartridge 200 is preferably composed of the reservoir 210 and the dispensing unit 220. The reservoir 210 may be suitably made of a plastic material which is dielectric, and also deformable according to the contents of the liquid composition. The reservoir 210 may be made by the same resilient material, or combination of a rigid material and resilient material. An example of commercially available material suitable for providing the reservoir is the laminated film of VM-PET (Vacuum Metalised Polyethylene Terephthalate) having a thickness of 12 microns and LLDPE (Linear Low Density Polyethylene) having a thickness of 60 microns. Commercially available films are GLAE by Toppan for VM-PET, and FCS by Tocello for LLDPE.

Figure 2:
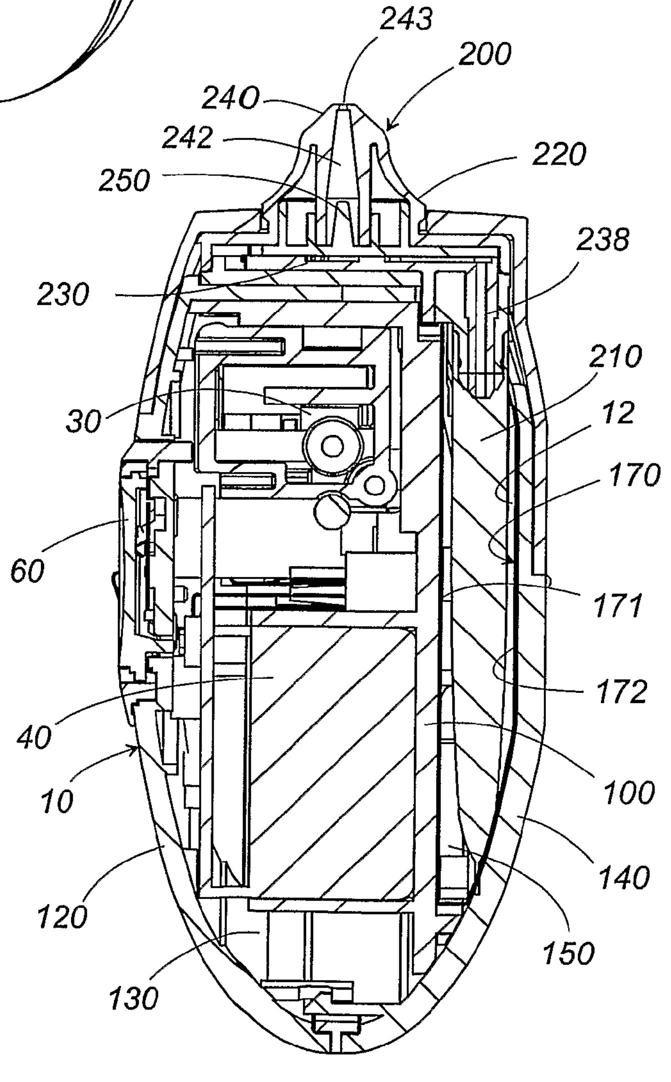
FIG. 2 is a vertical section of the device of FIG. 1.
Figure 3:
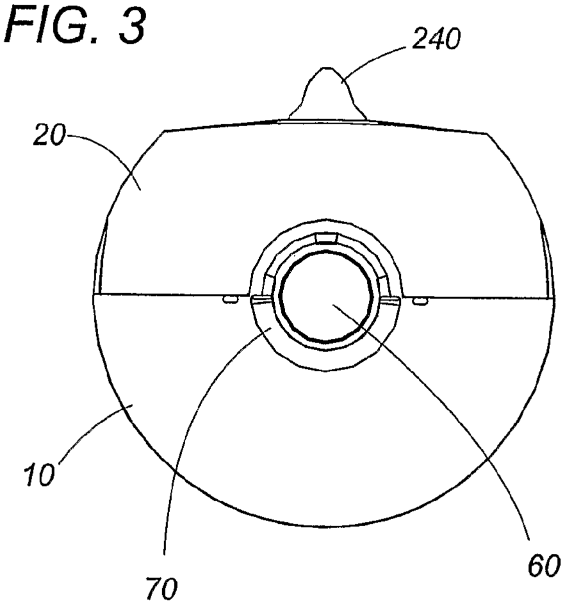
FIG. 3 is a front view of the device of FIG. 1.
Figure 4:
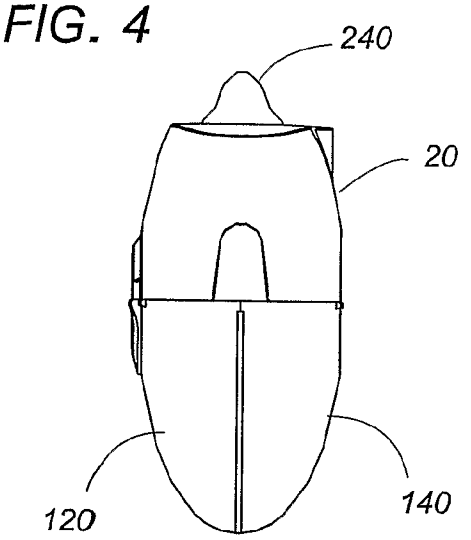
FIG. 4 is a side view of the above device.

As best shown in FIGS. 6 to 9, in an exemplary embodiment the dispensing unit 220 includes a pump 230 and a nozzle 240 which are integrated into a single structure. The pump 230 is a gear pump having a flat base 231 molded from a plastic material and formed with a plug 232 for detachable insertion into a fitment 212 secured to a mouth of the reservoir 210. The pump 230 includes a metal plate 270 mounted in the base 231 of the molded plastic. The metal plate 270 is formed in its upper surface with a pump chamber receiving a pair of intermeshing gears 234, an inflow channel 236 extending from within the plug 232 to the chamber, and an outflow channel 237 extending from the chamber to the nozzle 240. The pump chamber as well as the channels 236 and 237 are sealed by an emitter electrode 250 secured between the base 231 and the nozzle 240. The gears 234 are arranged to have their individual rotation axes extending perpendicular to the plane of the base 231, realizing a flat pump structure sufficient to be capable of being disposed between the reservoir 210 and the nozzle 240 only at a minimum extra dimension with respect to the height or length of the dispensing unit 220. One of the gears 234 is coupled to a joint 238 projecting on the lower face of the base 231 for detachable driving connection with the motor 30 disposed within the housing 10. As the gears are driven to rotate, the liquid composition is sucked up from the reservoir 210 through the inflow channel 236 and expelled through the outflow channel 237 to the nozzle 240. Preferably, the nozzle 240 is molded from a compatible plastic material as the base 231 to have an internal nozzle pathway 242 extending from the bottom center to an apex 243, as best shown in FIG. 2.

The emitter electrode 250 is disposed between the base 231 of the pump 230 and the bottom 241 of the nozzle 240 in order to apply the high voltage to and charge the liquid composition being dispensed through the nozzle 240. In an exemplary embodiment, the emitter electrode 250, which is connected to receive the high voltage from the high voltage generator 40 in the housing 10, includes a center antenna 251 and a coaxial cylinder 252. The center antenna 251 extends into the nozzle pathway 242 to charge the liquid composition being dispensed in cooperation with the cylinder 252 that is provided to surround the nozzle pathway 242 to avoid the undesired corona discharging for suitable electrostatic spraying. The top end of the center antenna 251 is receded from the apex 243 of the nozzle 240 to give a sufficient insulation distance therebetween.

Figure 11:
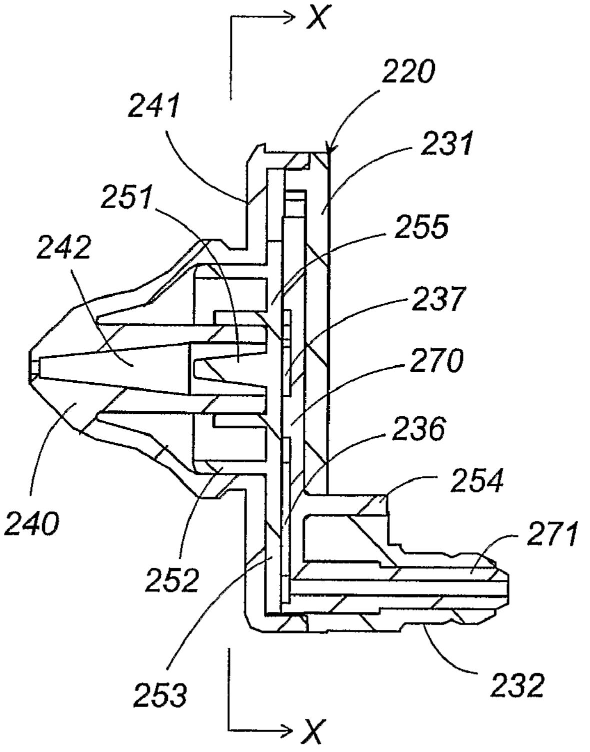
FIG. 11 is a sectional view of the dispensing unit.
Figure 12:
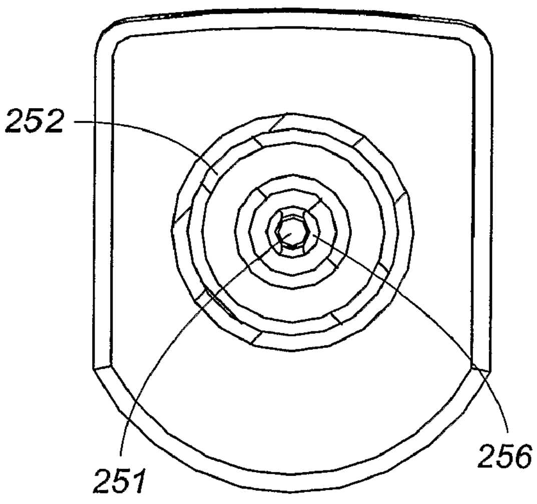
FIG. 12 is a section take along line X-X of FIG. 11.
Figure 13:
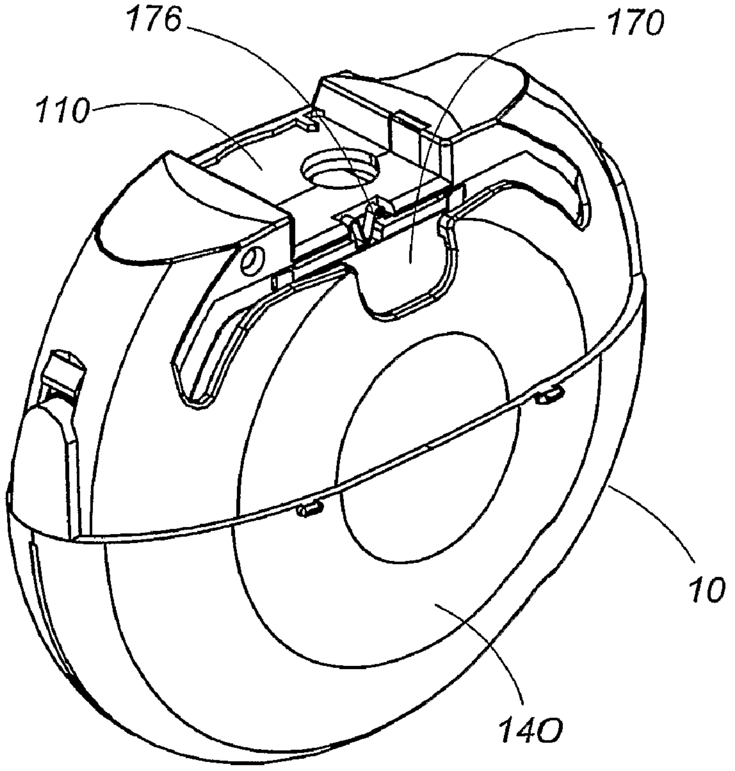
FIG. 13 is a perspective view of a main body housing of the device.
Figure 14:
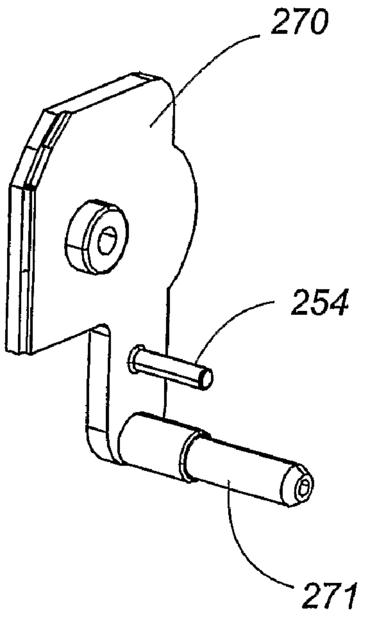
FIG. 14 is a perspective view of a metal plate forming a part of the dispensing unit.
Figure 15:
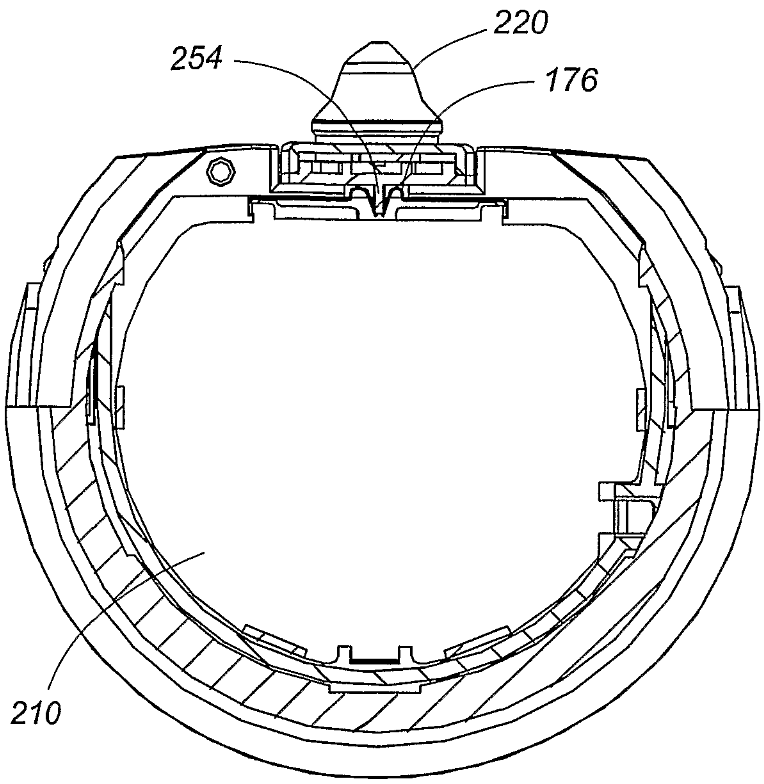
FIG. 15 is a partial rear section showing an electrical connection between the dispensing unit and a voltage terminal provided on the side of the housing.
Figure 16:
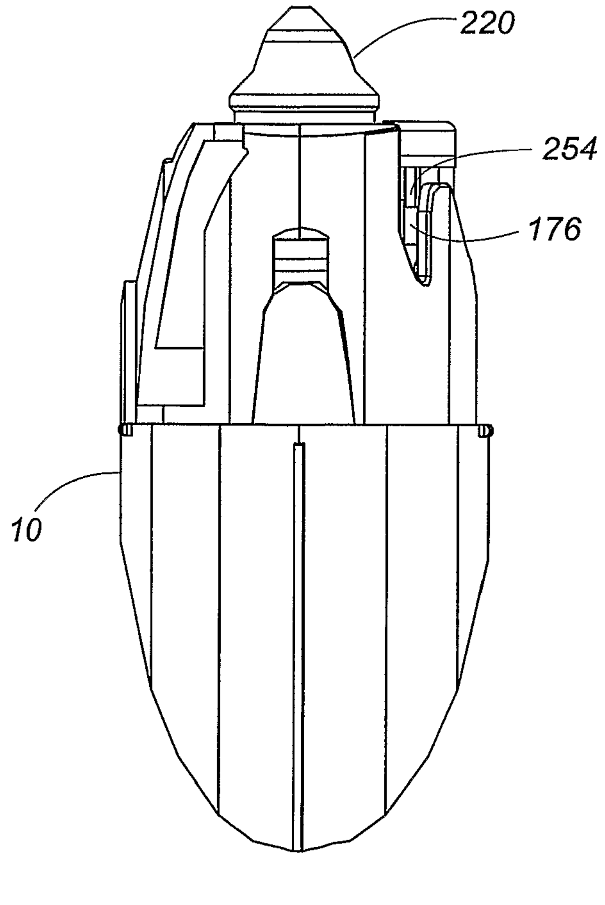
FIG. 16 is a partial vertical section showing the electrical connection between the dispensing unit and the voltage terminal.

As best shown in FIGS. 13 to 16, the metal plate 270 is formed integrally with a pin 254 which projects through the base 231 for detachable electrical connection with a voltage terminal 176 provided on the side of the housing 10 to relay the high voltage to the emitter electrode 250. Turning back to FIGS. 6 and 7, the emitter electrode 250 also includes a flat bottom 253 that is placed over the base 231 to seal the pump. The flat bottom 253 and the metal plate 270 are cooperative to charge the liquid composition within the pump in order to avoid undesired current flow within the liquid composition in the pump which would otherwise cause deterioration of the liquid composition. As shown in FIGS. 11 and 12, the cylinder 252 is connected to the antenna 251 by a rim 255. The rim 255 is formed with a plurality of slots 256 that communicate with the outflow channel 237 of the pump for passing the liquid composition from the pump to the nozzle pathway 242.

Figure 5:
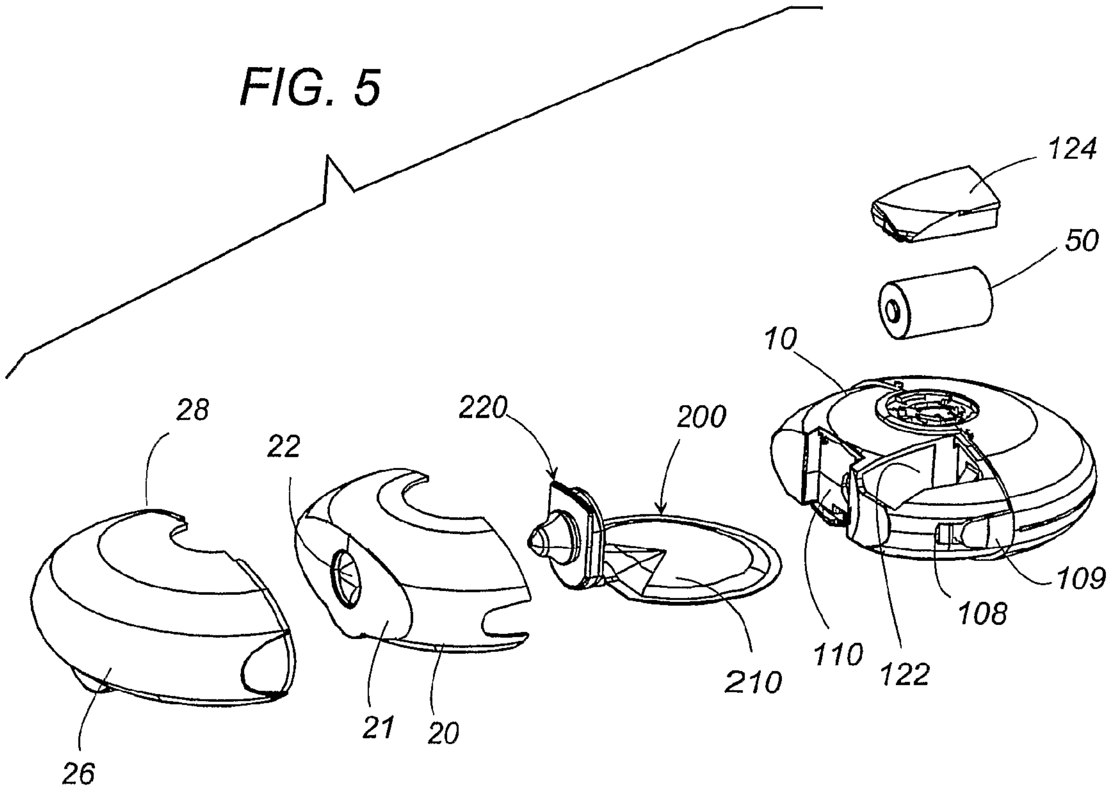
FIG. 5 is an exploded perspective view of the above device.
Figure 6:
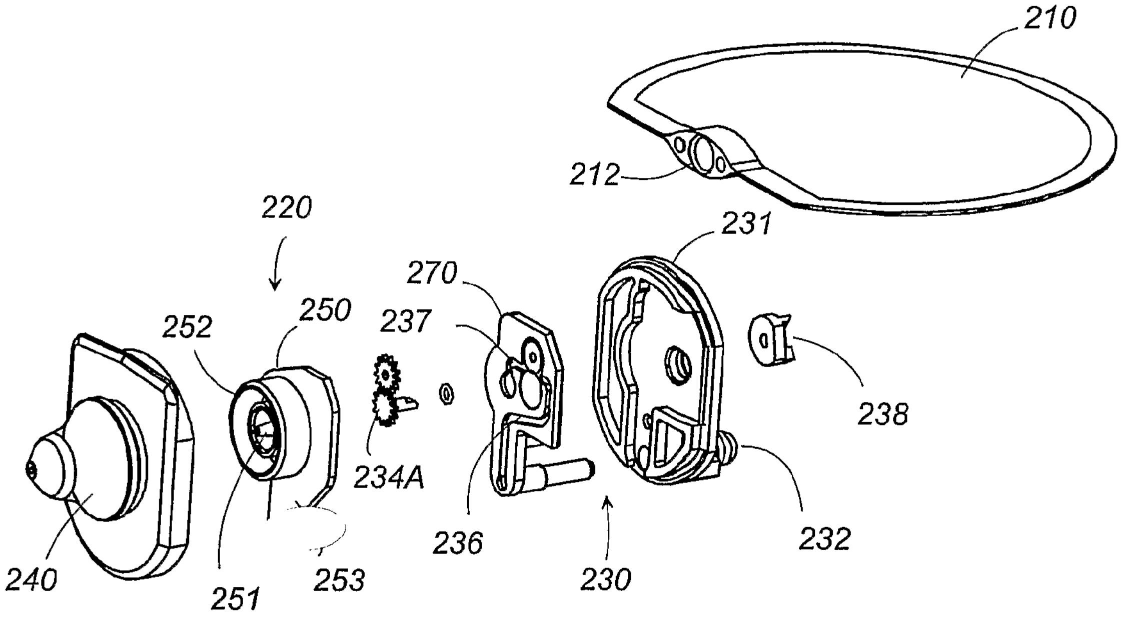
FIGS. 6 to 8 are respectively exploded perspective views of a removable cartridge utilized in the above device.
Figure 7:
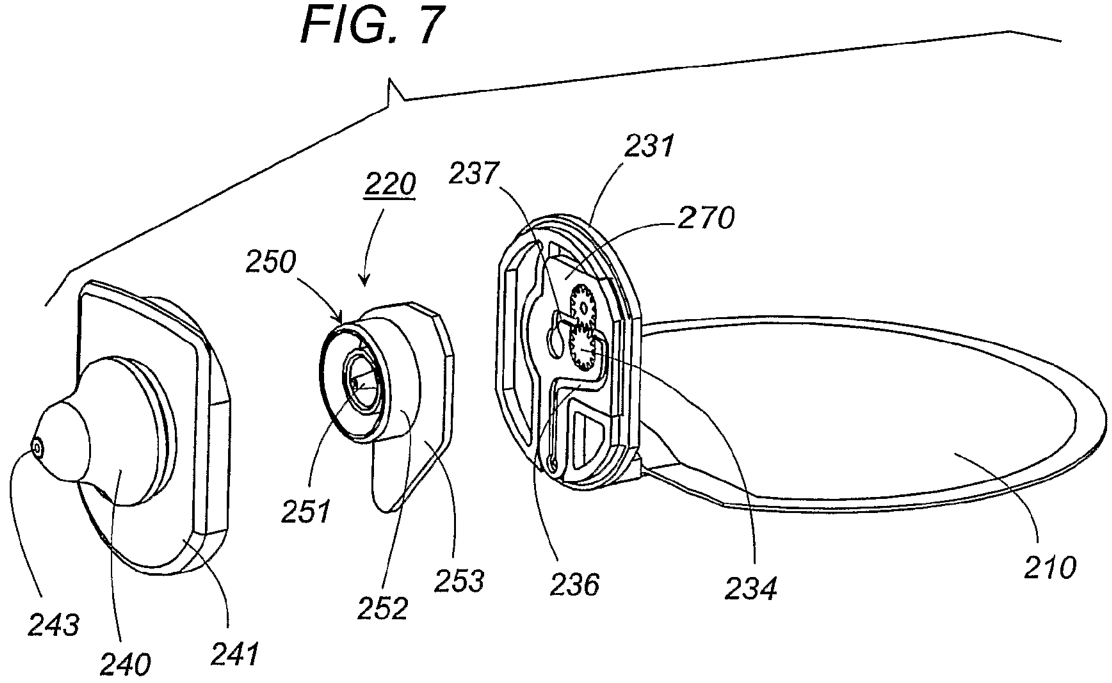
Figure 8:
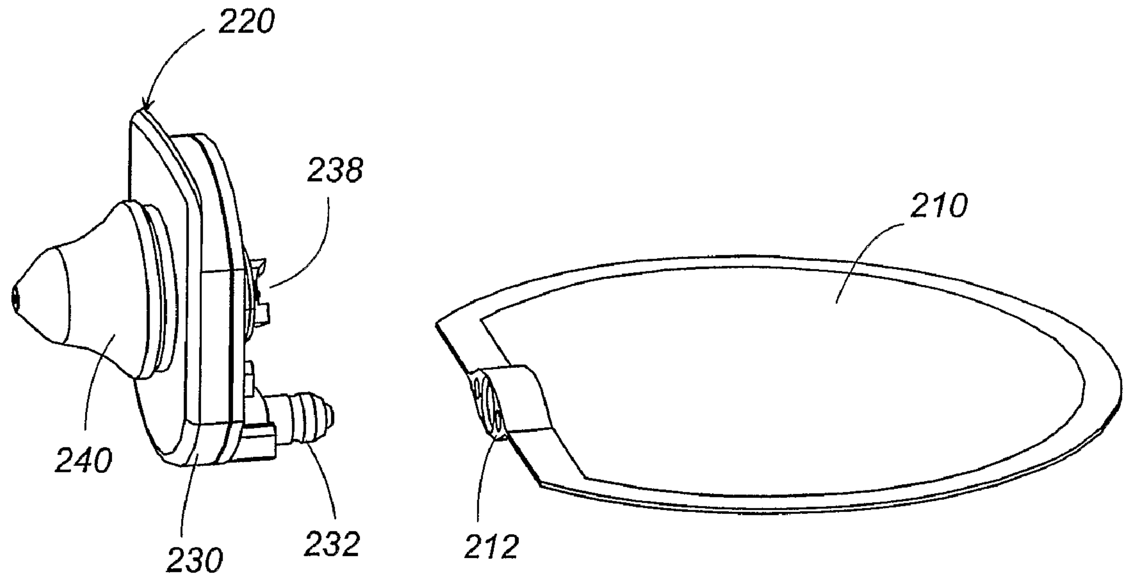
Figure 9:
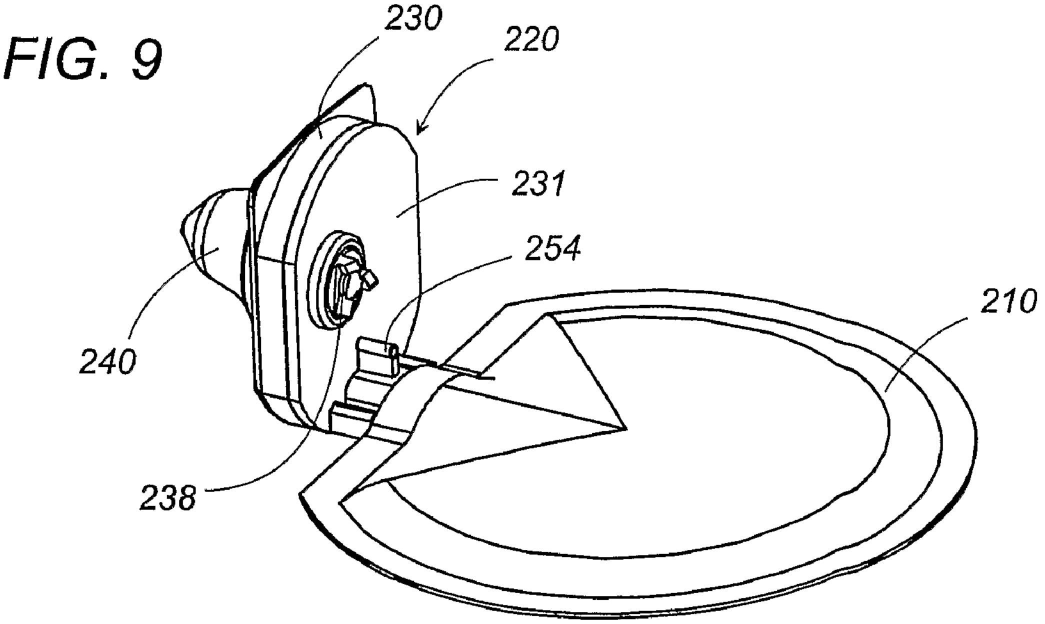
FIG. 9 is a perspective view of the cartridge of FIG. 8 as viewed from the bottom.
Figure 10:
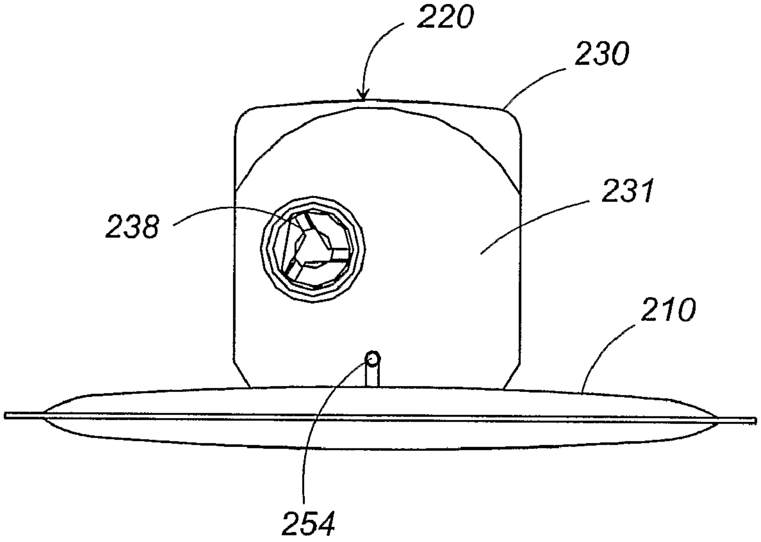
FIG. 10 is a bottom view of the cartridge of FIG. 9.
Figure 17:
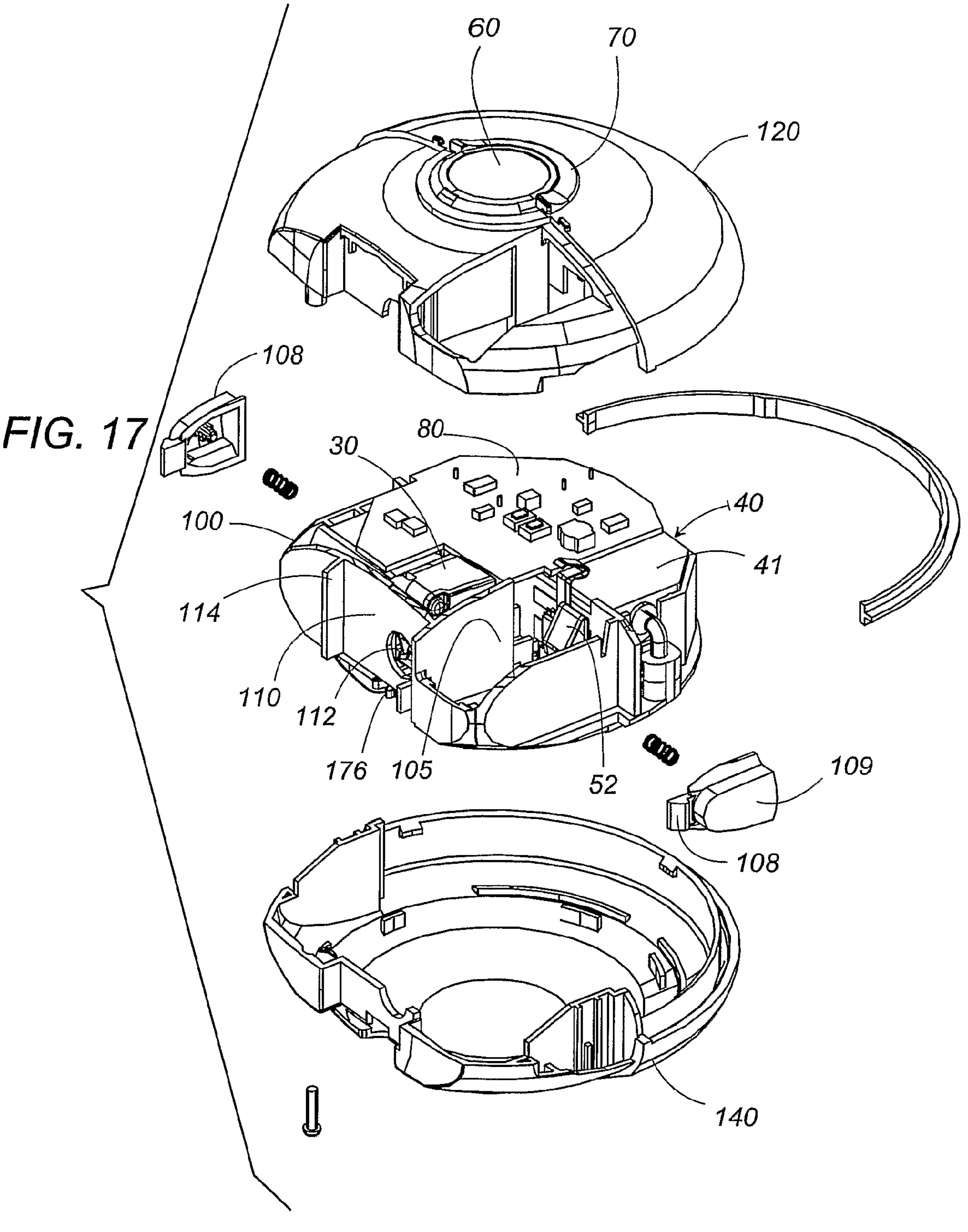
FIG. 17 is an exploded perspective view of the housing of the device.
Figure 18:
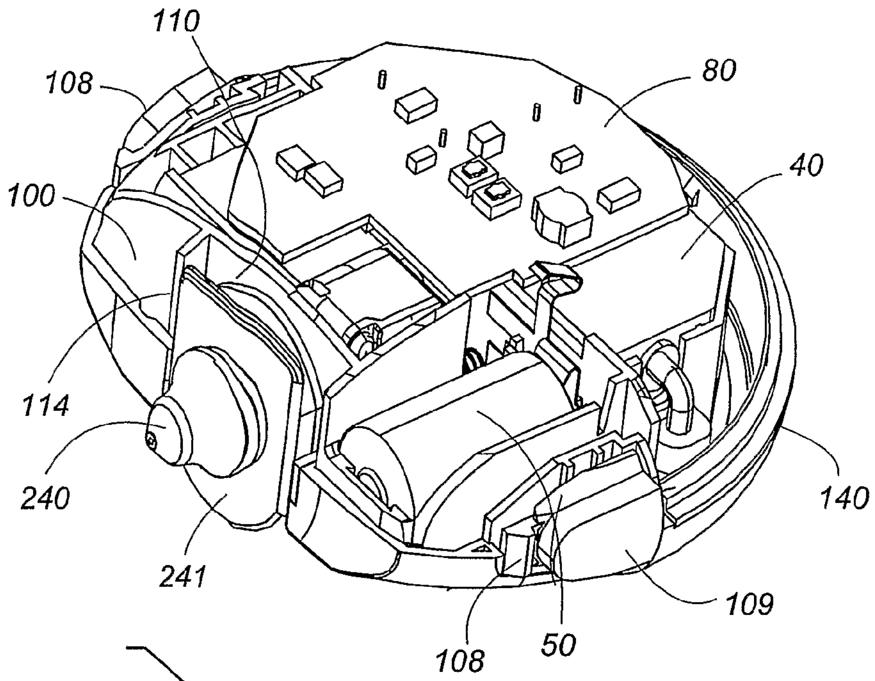
FIG. 18 is a perspective view of the device shown with a front shell of the housing removed.
Figure 19:
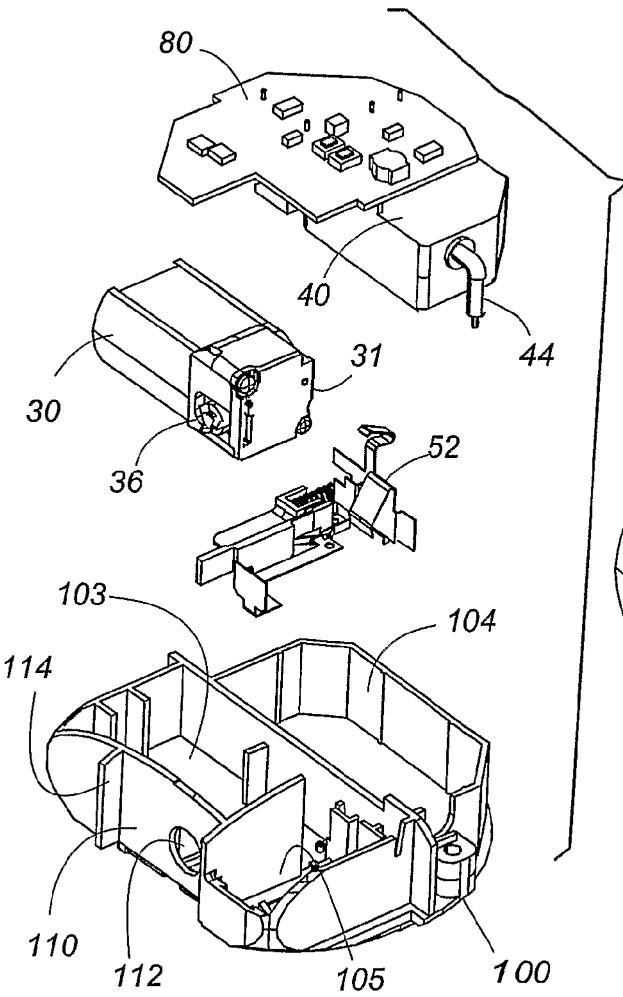
FIG. 19 is an exploded perspective view illustrating a center frame of the housing, a motor and a high voltage generator mounted on the frame in accordance with the preferred embodiment of the present invention.
Figure 20:
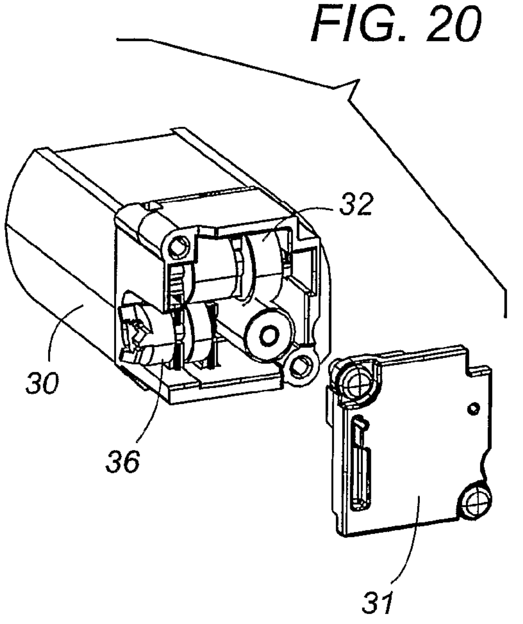
FIG. 20 is an exploded perspective view showing the motor and its associated parts accommodated within the housing in accordance with the preferred embodiment of the present invention.

As shown in FIG. 17, the housing 10 may be shaped into a generally flat disc, and thus basically composed of a center frame 100, a front shell 120, and a rear shell 140 all being molded from a dielectric plastic material and assembled together into a unitary structure to form a front compartment 130 and a rear compartment 150 on opposite faces of the frame 100, respectively behind the front and rear shells. When taking such generally flat disc shape, the front compartment 130 accommodates therein the motor 30, the battery 50, and the high voltage generator 40 which are all supported on the frame 100, while the rear compartment 150 constitutes the concavity 12 for receiving the reservoir 210. The frame 100 is formed on its front face with individual sections 103, 104, and 105 respectively for mounting the motor 30, the high voltage generator 40, and the battery 50, as shown in FIGS. 18 and 19. The motor 30 is received in the section 103 together with a gearbox 31. The high voltage generator 40 is composed of a transformer 41 and various electric components mounted on a printed board 80. The transformer 41 is packed into an insulated module fitted in the section 104. In that the transformer 41 occupies much more space than the motor 30 and battery 50, the housing is designed to arrange the transformer 41, the motor 30, and the battery 50 in compact. That is, the transformer 41 is accommodated within the lower part of the front compartment, while the motor 30 and the battery 50 are accommodated within the upper part of the front compartment in side-by-side relation with each other such that the motor and the battery are arranged in stack with the transformer with respect to a vertical axis of the housing 10. The section 105 receives, in addition to the battery 50, a terminal fixture 52 having leads for electrical connection of the battery 50 to the motor 30 and the high voltage generator 40 through a power switch 60 and a control circuit formed on the printed board 80. As shown in FIG. 20, the gearbox 31 includes a reduction gear set 32 through which the motor output is transmitted to an actuator 36 provided for detachable driving connection to the joint 238 of the pump 230 on the side of the cartridge 200. Preferably, the actuator 36 is disposed immediately below a mount 110 formed at the upper end of the frame 100 and is accessible through an opening 112 in the mount 110, as shown in FIGS. 22 and 23. The mount 110 is somewhat recessed for retaining the dispensing unit 220 thereon when the cartridge 200 is attached to the housing 10. The mount 110 is cooperative with adjacent side walls 114 to define a positioning means for the cartridge. Preferably, a pair of hooks 108 is attached on the opposite sides of the frame 100 to constitute a positioning means for detachably holding the inner cover 20 on the housing 10. The hook 108 has a release button 109 which releases the inner cover 20 upon being pressed. As seen in FIGS. 1 and 5, the inner cover 20 may have a flat top 21 formed with a center window 22 through which the nozzle 240 projects when the inner cover 20 is placed over the top half of the housing 10 with the cartridge 200 attached to the housing 10. The periphery of the window 22 constitutes a retainer ring that holds the flat nozzle bottom 241 on the mount 110 at the upper end of the housing 10. As shown in FIG. 21, the front shell 120 is formed with a window 122 which communicates with the section 105 for replacement of the battery 50. Thus, the battery 50 can be easily replaced by simply removing the inner cover 20 as well as a lid 124 of the window 122. The lid 124 may be eliminated from the device for simplicity.

Figure 24:
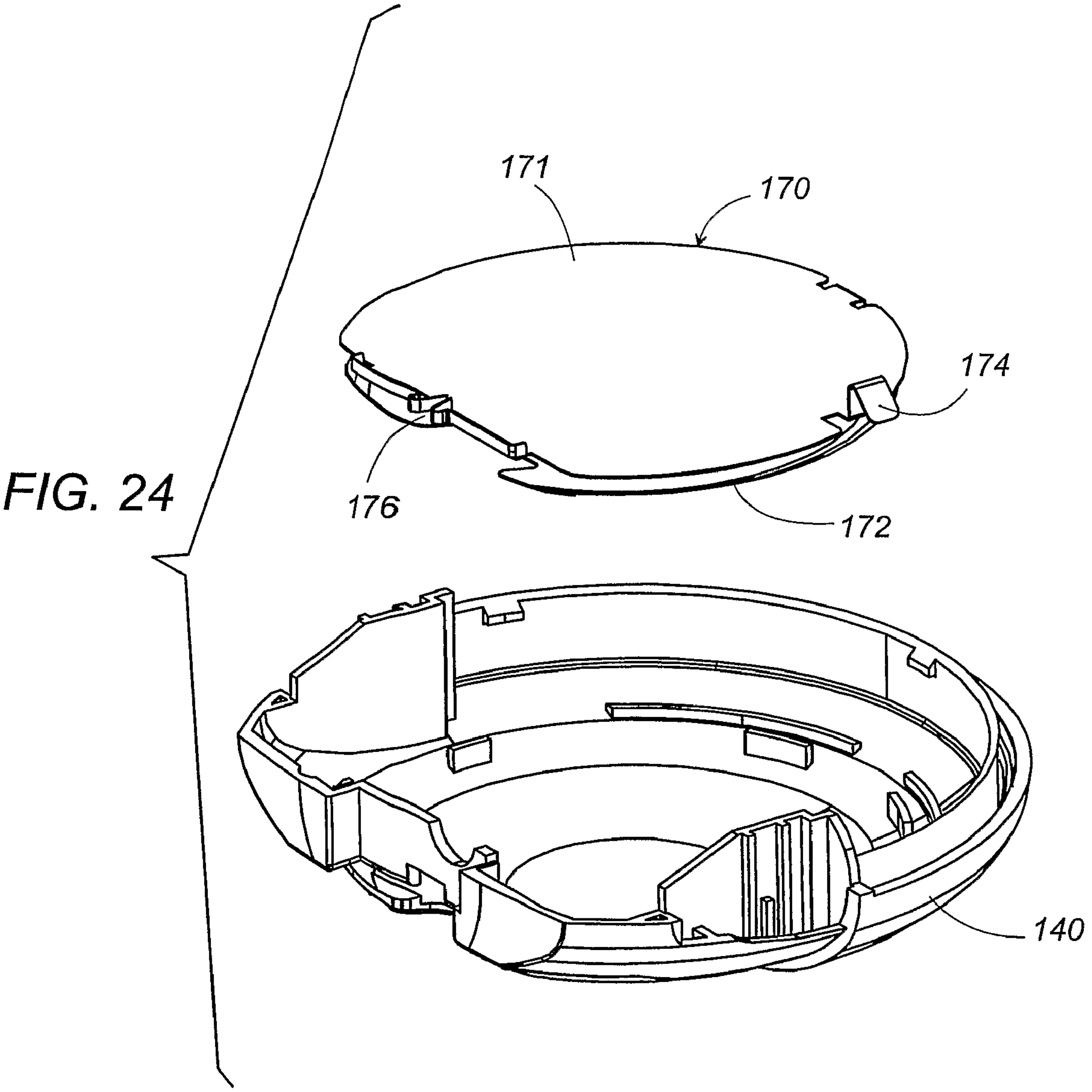
FIG. 24 is an exploded perspective view of parts forming a field electrode and associated parts of the above device.

Accommodated within the rear compartment 150 is a field electrode 170 which surrounds the reservoir 210 to give the same electrical potential to the liquid composition within the reservoir 210 and to the liquid composition within the dispensing unit 220 for keeping the entire liquid composition free from seeing the electric current which may deteriorate the liquid composition. Such deterioration is particularly seen in emulsion compositions and compositions having particles dispersed therein. As best shown in FIGS. 23 and 24, the field electrode 170 is preferably composed of a first plate 171 and a second plate 172 both made of an electrically conductive metal and shaped to define therebetween the concavity 12 surrounding the entire area of the reservoir 210. The plates 171 and 172 are electrically connected to each other at their peripheries, and are secured to the frame 100 and the rear shell 140. In order to receive the high voltage, the plate 171 is formed to have a lug 174 which extends through the frame 100 for electrical connection with a terminal 44 of the high voltage generator 40. The plate 171 is also formed with the voltage terminal 176 in the form of a spring catch for detachable connection with the pin 254 of the dispensing unit 220, as explained hereinabove.

It is noted in this connection that the metal plate 270 and the 250 of the dispensing unit 220 are electrically connected to the field electrode 170 and therefore act as additional field electrode covering the pump. Also, the metal plate 270 is formed with a metal tube 271 which is inserted into the plug 232 to charge the liquid composition within the plug, and therefore acts also as a further field electrode. Thus, the liquid composition is electrically charged along the entire path from the reservoir 210 to the nozzle 240. Instead of using the metal tube 271, it is equally possible to provide an extension which extends from at least one of the plates 171 and 172 and projects outwardly from the concavity to cover the plug 232 and the adjacent part of the dispensing unit.

Figure 25:
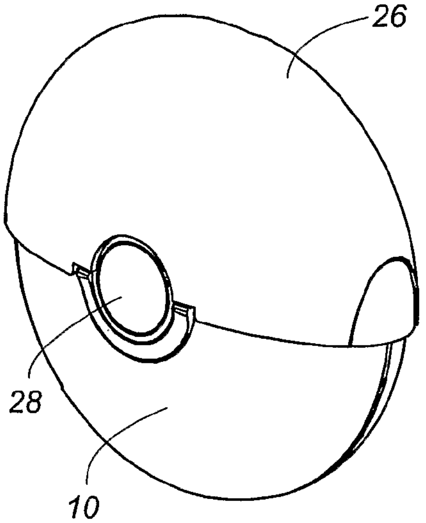
FIG. 25 is a perspective view of the above device with an outer cover attached.
Figure 26:
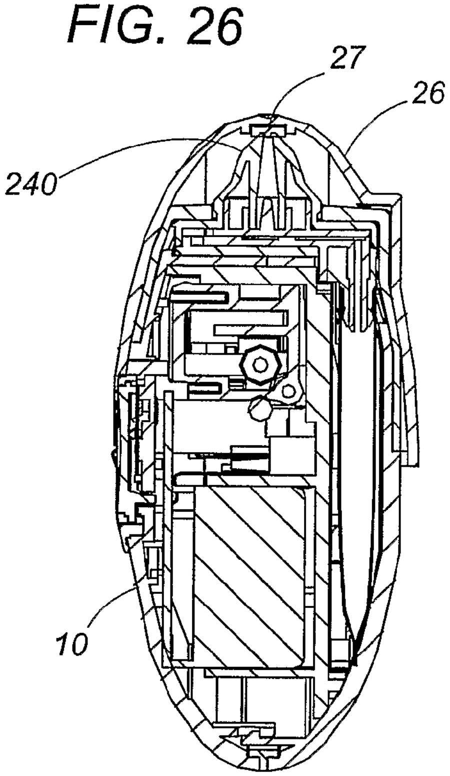
FIG. 26 is a vertical section of the above device with the outer cover attached.

Preferably, when the outer cover 26 is fitted over the housing 10, as shown in FIGS. 25 and 26, a sealing rubber 27 at the inner upper end of the outer cover 26 comes into contact with the nozzle 240. The outer cover 26 is also formed with tabs 28 one of which conceals therebehind the power switch 60 to keep the device inoperative. Also, the outer cover 26 conceals the release buttons 109 therebehind to prevent accidental detachment of the inner cover from the housing 10.

Figure 27:
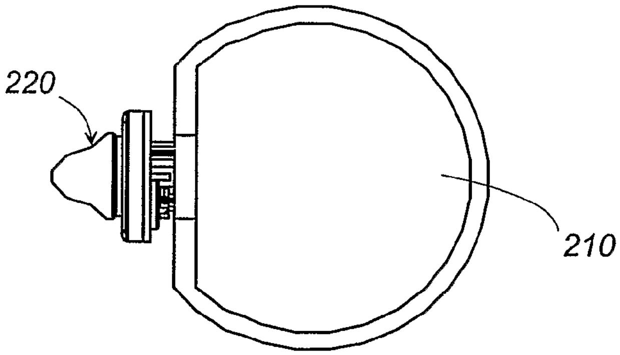
FIG. 27 is a plan view of the cartridge.
Figure 28:
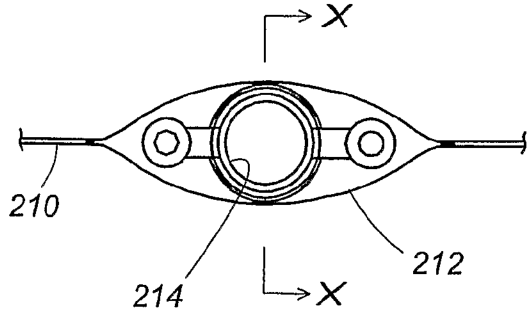
FIG. 28 is a front view of a fitment attached to a reservoir of the cartridge.
Figure 29:
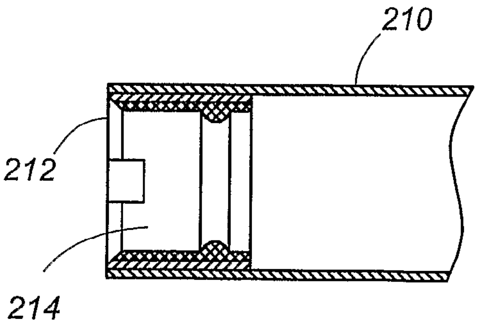
FIG. 29 is a cross section taken along line X-X of FIG. 28.

With reference to FIGS. 27 to 29, the cartridge 200 is again explained in details with respect to geometrical configuration of the reservoir 210. One exemplary embodiment of the reservoir as shown as 210 is made from a deformable plastic material into a flat bag which has a planar configuration of a segment of an approximate circle and has a mouth to which the fitment 212 is attached. The fitment 212 is molded from a plastic material to have a socket 214 for removably receiving the plug 232 of the dispensing unit 220. In detail, the reservoir 210 is shaped into the segment of circle defined between a chord and a circumference of an approximate circle greater than a circumference of a semicircle. The mouth or the fitment 212 is located at a center of the chord such that the distance from the mouth to any point of the circumference of the circle can be made approximately the same, providing smooth sucking up of the liquid composition from the reservoir and deforming according to the amount of liquid composition left in the reservoir, such that residue left in the end can be kept to a minimum.

Figure 30:
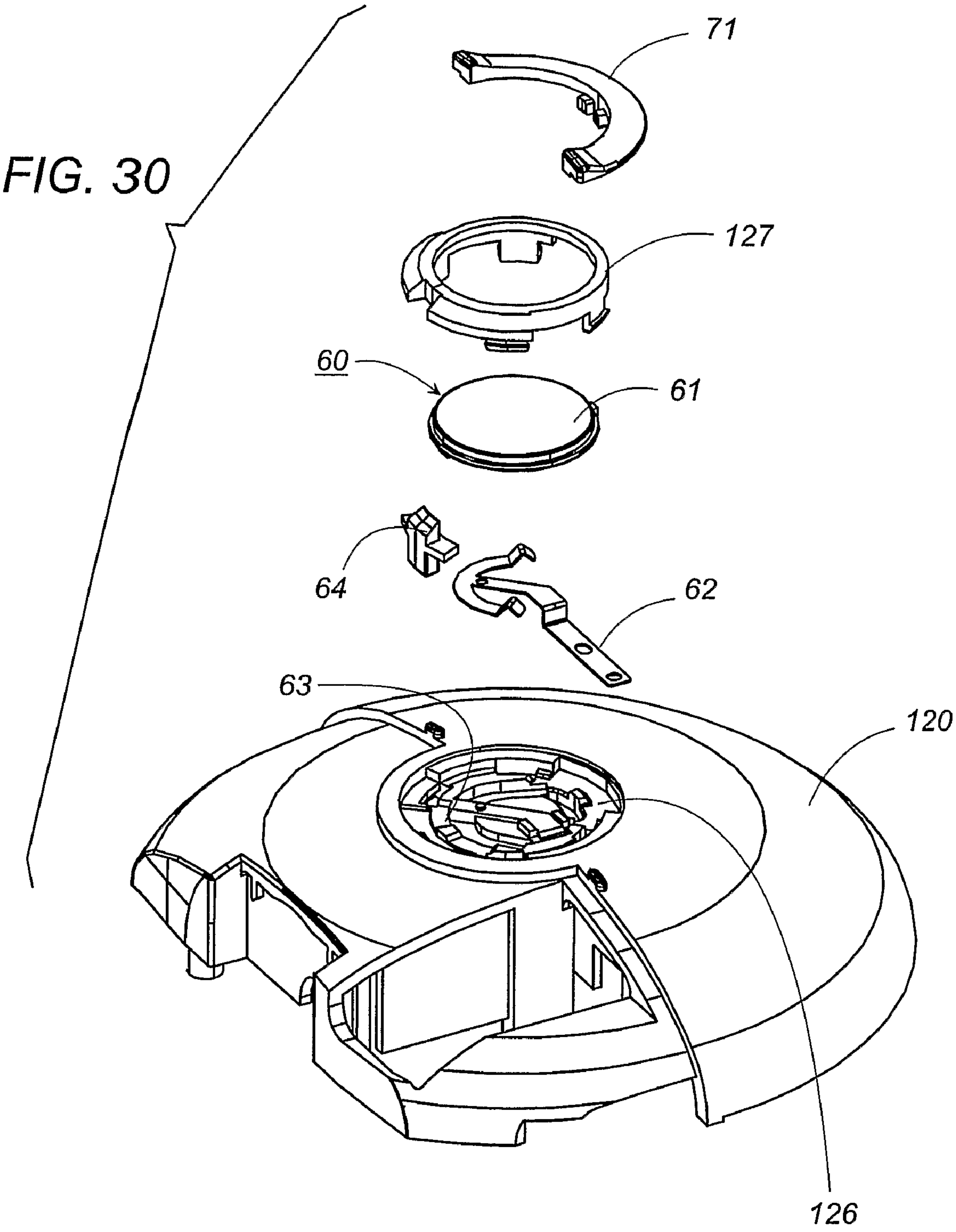
FIG. 30 is an exploded perspective view illustrating a switch, a selector, and associated parts of the device.

Referring to FIG. 30, the power switch 60 preferably includes a switch knob 61 and a switch contact 62 disposed within a center cavity 126. The switch knob 61 is held within the cavity 126 by means of a retainer ring 127 to be capable of being depressed against a spring bias, and energizes the motor 30 and the high voltage generator 40 upon being depressed. A light-emitting-diode (LED) 63 disposed in the cavity 126 is energized in response to the knob 61 being depressed to issue a light through a transparent cover 64 for indication of the operation.

Figure 31A:
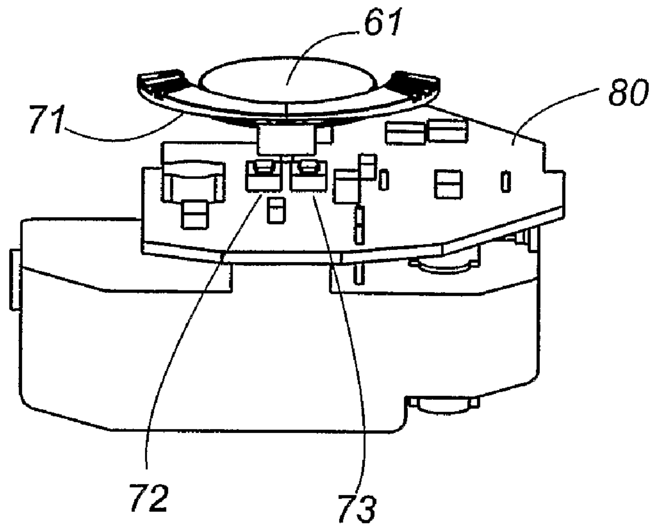
FIGS. 31A to 31C illustrate different positions of the selector, respectively.
Figure 31B:
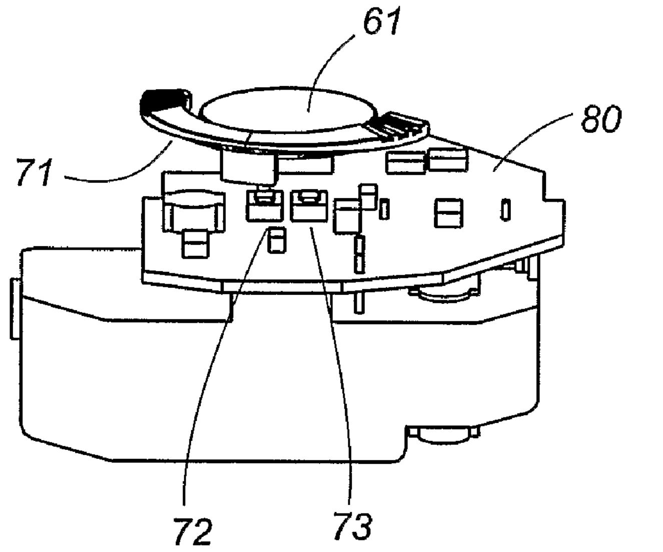
Figure 31C:
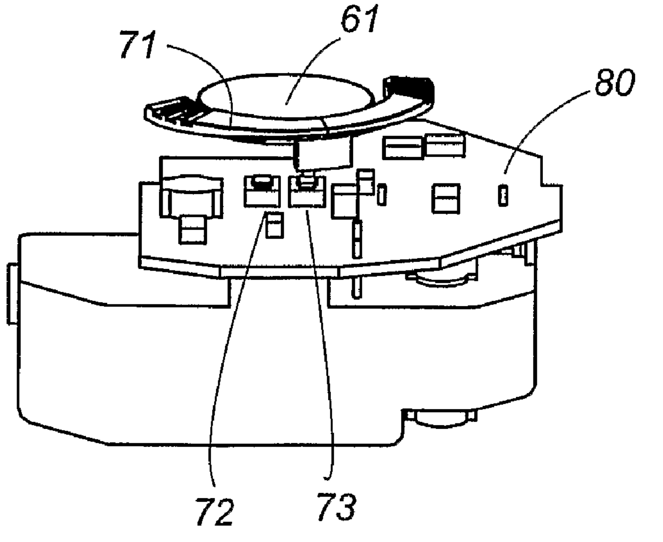

In an exemplary embodiment, the device also includes a selector 70 for selecting one of three modes, i.e., a lock mode for disabling the operation, a spraying mode for enabling the liquid composition to be electrostatically sprayed, and a dripping mode for enabling the liquid composition to be dispensed out of the nozzle without being electrostatically charged. The selector 70 includes a handle 71 which is rotatable around the ring 127 for selecting one of three positions, i.e., a lock position, a spraying position, and a dripping position, as shown in FIGS. 31A to 31C, respectively defining the above lock mode, the spraying mode, and the dripping mode. In the lock position of FIG. 31A, the handle 71 has its portion engaged with the switch knob 61 to prohibit it from being pressed, thereby disabling the operating of the pump as well as the high voltage generator. The selector 70 also includes tact switches 72 and 73 which are arranged on the printed board 80 to be actuated selectively depending upon the position of the handle 71. In the spraying mode of FIG. 31B, the tact switch 72 is activated such that the pump 230 and the high voltage generator 40 are simultaneously activated upon the switch knob 61 being pressed. In the dripping mode of FIG. 31C, the tact switch 73 is activated such that only the pump 230 is activated upon the switch knob 61 being pressed. Although not clearly seen in the figures, the device may further include an indicator showing which one of the dripping and spraying modes is selected for easy confirmation by the user. Such indicator is preferred to be disposed around the selector handle 71.

Figure 32:
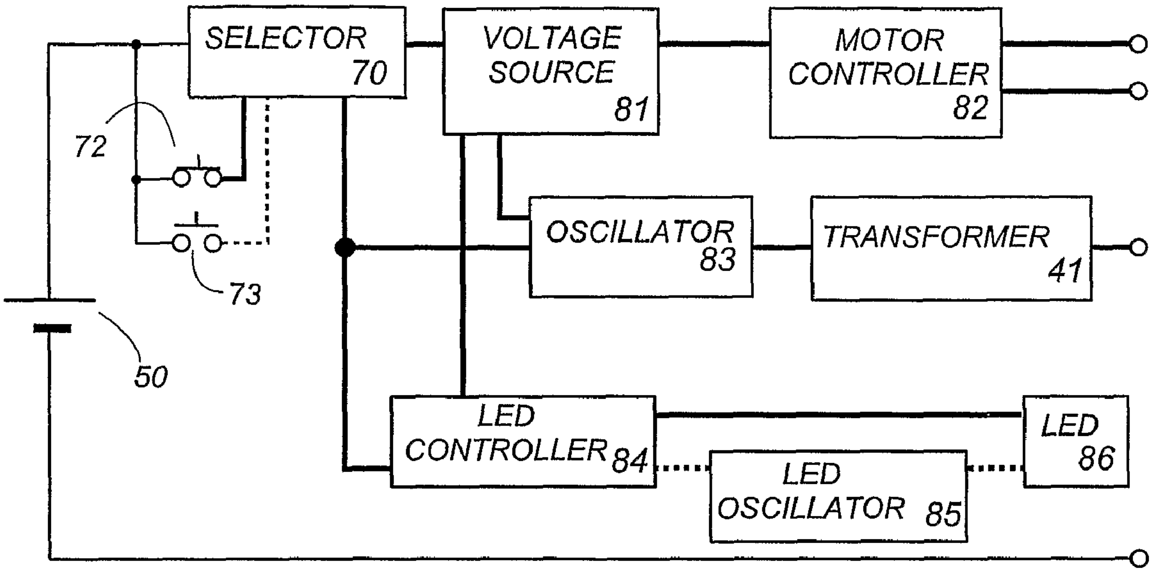
FIGS. 32 and 33 are block diagrams respectively illustrating the operation of a spraying mode and a dripping mode given to the device.
Figure 33:
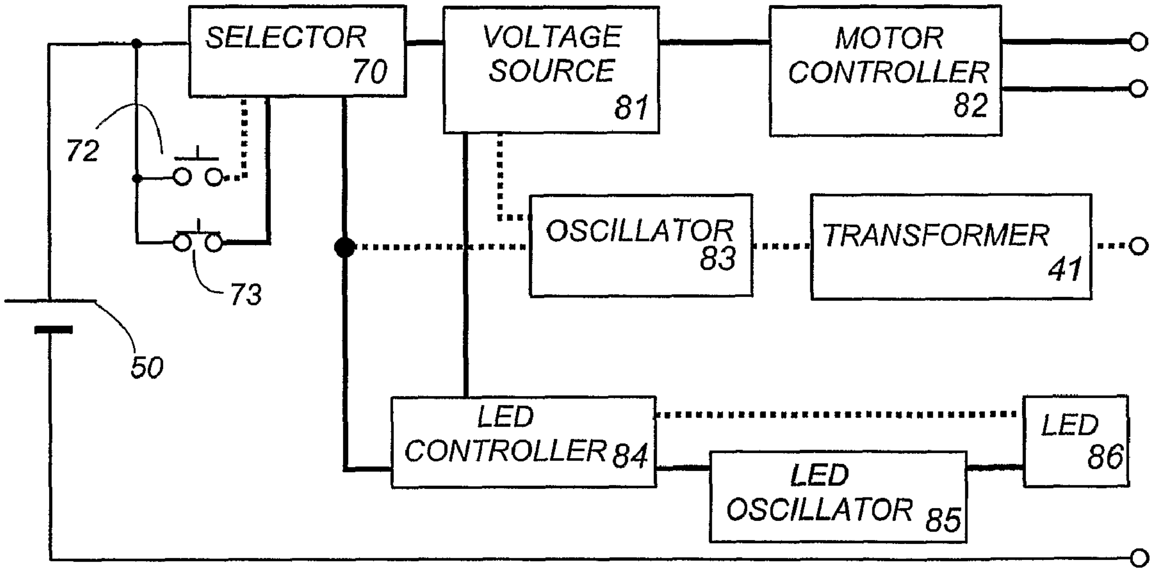

The above operation will be explained also with reference to FIGS. 32 and 33. When the tact switch 72 is turned on by the selector handle 71, the pressing of the knob 61 energizes a voltage source 81, a motor controller 82 and at the same time an oscillator 83 for the transformer 41, thereby activating the motor 30 to operate the pump 230, while applying the high voltage to charge the liquid composition. When, on the other hand, the tact switch 73 is turned on by the selector handle 71, the pressing of the knob 61 energizes the voltage source 81 and the motor controller 82 only for operating the pump without applying the high voltage to the liquid composition. Thus, the user can easily drip the liquid composition by simply manipulating the selector prior to initiating the electrostatic spraying, assuring enhanced convenience of handling the device. The voltage source 81, the motor controller 82, and the oscillator 83 are formed on the printed board 80.

Figure 34A:
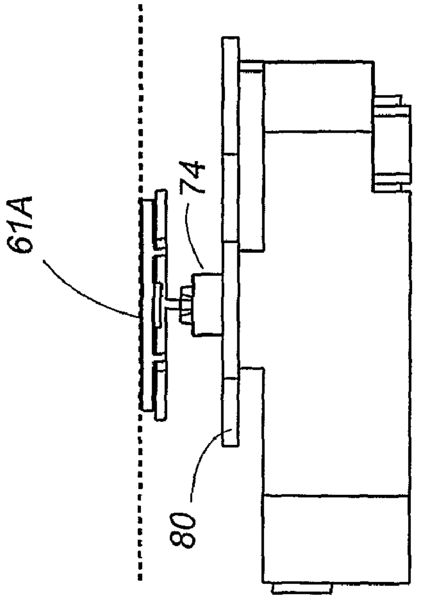
FIGS. 34A to 34C illustrate different positions of a switch for making an analogous function of the selector in accordance with another exemplary embodiment of the present invention.
Figure 34B:
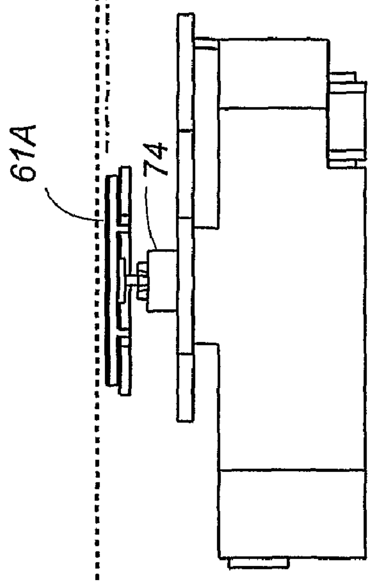
Figure 34C:
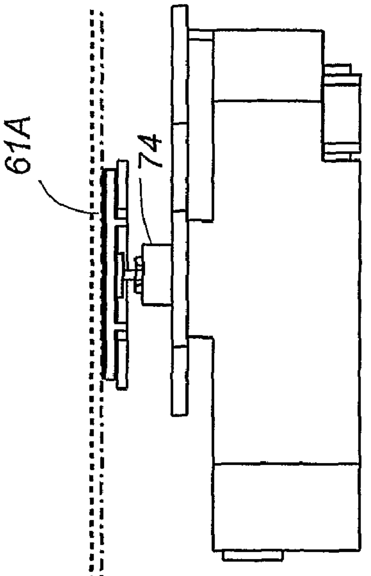

FIGS. 34A to 34C illustrate another scheme of selecting the dripping mode and the spraying mode. In this modification, a tact switch 74 of press-responsive type is cooperative with the switch knob 61A to constitute the power switch added with the function of the selector. That is, the tact switch 74 gives three positions, i.e., an off position of FIG. 34A, a spray mode position of FIG. 34B, and a drip mode position of FIG. 34C. In the off position, the switch 74 is not actuated to disable the operation of the pump as well as the high voltage generator. When the knob 61A is pressed to a small extent to correspondingly depress the switch 74, the spraying mode is selected to energize the pump 230 as well as the high voltage generator 40 for making the electrostatic spraying of the liquid composition. Upon the knob 61A being pressed to a further extent, the switch 74 is correspondingly depressed to select the dripping mode to activate only the pump 230 for dispensing the liquid composition without the electric charge. Thus, the user can easily select the mode by simply varying the pressure applied to the switch knob 61A. Alternatively, the dripping mode and the spraying mode may be assigned respectively to the depression of the small extent and to that of the further extent.

All documents cited in the detailed description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. An electrostatic device configured and disposed to electrostatically charge and dispense a liquid composition from a supply to a dispensing point, wherein the device comprises: an actuator; a high voltage generator to provide a high voltage; a power source to activate said actuator and said high voltage generator; a reservoir to contain the supply of said liquid composition; and a dispensing unit comprising: a pump in immediate downstream relation with the reservoir for supplying the liquid composition from the reservoir, said pump being mechanically connected to said actuator to be driven thereby; an emitter electrode to electrostatically charge the liquid composition, the emitter electrode being electrically connected to said high voltage generator; and a nozzle to dispense the liquid composition, said nozzle being disposed at the dispensing point; wherein the device further comprises a field electrode surrounding the reservoir, said field electrode being connected to said high voltage generator; and wherein the reservoir is configured to provide a removable cartridge, said reservoir being formed separately from the field electrode, and wherein the emitter electrode and field electrode provide the entire liquid composition with more or less a common electric potential; said device includes a housing carrying said actuator, said high voltage generator, and said power source, said housing being formed with a concavity for detachably receiving said reservoir, said field electrode being incorporated in said housing around said concavity, and said reservoir being coupled to said dispensing unit and is cooperative therewith to define said cartridge, wherein said field electrode is in shaped to surround the reservoir.

2. The device as set forth in claim 1, wherein said housing incorporates a motor which drives said actuator for operating said pump;

said housing further incorporating therein a frame which mounts said motor as well as said high voltage generator, said frame dividing the interior space of said housing into a front compartment and a rear compartment, said front compartment accommodating said motor and said high voltage generator, and said rear compartment defining said concavity for receiving said reservoir, said housing comprising a front shell and a rear shell, said front shell being fitted over said frame to define therebetween said front compartment, said rear shell being fitted on said frame to define therebetween said rear compartment, said field electrode composed of a first plate secured to the frame and a second plate secured on the interior surface of said rear shell.

3. The device as set forth in claim 1, wherein said positioning means is a mount formed at the upper end of said housing on which said dispensing unit rests.

4. The device as set forth in claim 3, wherein said voltage terminal is located below an opening which is formed in the mount to permit the lower end of said emitter electrode to project through the opening for contact with said voltage terminal when said dispensing unit rests on said mount.

5. The device as set forth in claim 1, wherein said reservoir is deformable and made of a dielectric material.

6. The device as set forth in claim 1, wherein said pump is a suction pump having a drive element which is driven by said actuator to suck up said liquid composition from said reservoir and forces it out of said nozzle.

7. The device as set forth in claim 1, wherein said housing incorporates a motor which drives said actuator for operating said pump;

said housing further incorporating therein a frame which mounts said motor as well as said high voltage generator, said frame dividing the interior space of said housing into a front compartment and a rear compartment, said front compartment accommodating said motor and said high voltage generator, and said rear compartment defining said concavity for receiving said reservoir.

8. The device as set forth in claim 7, wherein said housing has a vertical axis that defines an upper end and a lower end along said vertical axis, and said high voltage generator comprising a transformer which is arranged in stack with said motor along said vertical axis within said front compartment.

9. The device as set forth in claim 8, wherein said front compartment accommodates a battery energizing the motor, said battery being arranged in a side-by-side relation with said motor in a direction perpendicular to said vertical axis and arranged in stack with said transformer along said vertical axis.

10. The device as set forth in claim 3, wherein an inner cover is provided to be detachably placed over a top portion of said housing, said inner cover having an opening through which said nozzle extends and defining around said opening a retainer which is placed against a portion of said dispensing unit to hold it in position on said mount.

11. The device as set forth in claim 10, wherein said housing is provided with a positioning means for engagement with said inner cover to retain it on the housing.

12. The device as set forth in claim 10, wherein said housing includes a front shell and a rear shell, in addition to said frame, said frame carrying said motor, said transformer, and a battery energizing said motor, said front shell being fitted over said frame to define therebetween said front compartment, said rear shell being fitted on said frame to define therebetween said rear compartment, said front shell being formed with a battery opening through which said battery is placed on said frame, said inner cover shielding said battery opening when attached to said housing.

13. The device as set forth in claim 12, wherein said housing is provided with a button for releasing said inner cover therefrom and with a switch knob for actuating said pump, an outer cover being provided to fit over said inner cover for concealing therebehind said dispensing unit, said button, and said switch knob.

14. The device as set forth in claim 1, wherein said field electrode is extended outwardly from said concavity to follow at least part of the dispensing unit for covering a flow path of said liquid composition from said reservoir to said nozzle.

15. The device as set forth in claim 1, wherein said dispensing unit further comprises a field electrode.

16. The device as set forth in claim 1, wherein said field electrode is composed of a first plate and a second plate both made of an electrically conductive metal and shaped to define therebetween said concavity surrounding the entire area of the reservoir.

17. The device as set forth in claim 1, wherein said housing is shaped into a flat disc.

* * * * *